United States Patent [19]

Haug et al.

[11] Patent Number: 4,969,948
[45] Date of Patent: Nov. 13, 1990

[54] HERBICIDAL AND PLANT GROWTH-REGULATING SUBSTITUTED PHENOXYPHENYLSULPHONYLAZOLES, COMPOSITIONS AND USE

[75] Inventors: Michael Haug, Bergisch Gladbach; Theodor Pfister, Monheim; Hans-Joachim Santel, Leverkusen; Robert R. Schmidt; Klaus Lürssen, both of Bergisch Gladbach; Harry Strang, Duesseldorf, all of Fed. Rep. of Germany

[73] Assignee: Bayer Aktiengesellschaft, Leverkusen, Fed. Rep. of Germany

[21] Appl. No.: 413,349

[22] Filed: Sep. 27, 1989

[30] Foreign Application Priority Data

Oct. 1, 1988 [DE] Fed. Rep. of Germany ....... 3833549

[51] Int. Cl.$^5$ .................... A01N 43/56; C07D 231/12
[52] U.S. Cl. ........................................... 71/72; 71/74; 71/92; 548/362; 548/375; 548/376
[58] Field of Search ...................... 548/362, 375, 376; 71/72, 74, 92

[56] References Cited

U.S. PATENT DOCUMENTS 4,778,914 10/1988 Cartwright ...................... 548/375

Primary Examiner—Robert W. Ramsuer
Attorney, Agent, or Firm—Sprung Horn Kramer & Woods

[57] ABSTRACT

Herbicidal and plant growth-regulating substituted phenoxyphenylsulphonylazoles of the formula

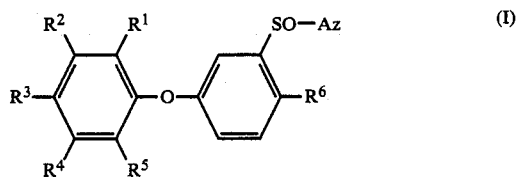

in which
  $R^1$ represents hydrogen, halogen, cyano or trifluoromethyl,
  $R^2$ represents hydrogen or halogen,
  $R^3$ represents halogen, cyano, trifluoromethyl, trifluoromethoxy or trifluoromethylsulphonyl,
  $R^4$ represents hydrogen or halogen,
  $R^5$ represents hydrogen or halogen,
  $R^6$ represents hydrogen, halogen, cyano, nitro or amino and
  Az represents optionally substituted azolyl.

13 Claims, No Drawings

HERBICIDAL AND PLANT GROWTH-REGULATING SUBSTITUTED PHENOXYPHENYLSULPHONYLAZOLES, COMPOSITIONS AND USE

The invention relates to novel substituted phenoxyphenylsulphonylazoles, processes for the preparation thereof, and the use thereof as herbicides and plant growth regulators.

It has been disclosed that certain phenoxyphenyl compounds, such as, for example, methyl 3-(2,4-dichlorophenoxy)-6-nitro-benzoate (Bifenox) are herbicidally active (cf. U.S. Pat. No. 3,652,645 and U.S. Pat. No. 3,776,715). However, the action of this previously known compound is not satisfactory in all respects.

Novel substituted phenoxyphenylsulphonylazoles of the general formula (I)

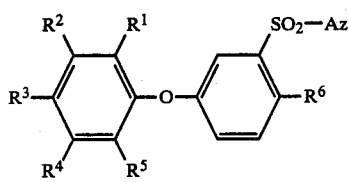

in which
R$^1$ represents hydrogen, halogen, cyano or trifluoromethyl,
R$^2$ represents hydrogen or halogen,
R$^3$ represents halogen, cyano, trifluoromethyl, trifluoromethoxy or trifluoromethylsulphonyl,
R$^4$ represents hydrogen or halogen,
R$^5$ represents hydrogen or halogen,
R$^6$ represents hydrogen, halogen, cyano, nitro or amino and
Az represents optionally substituted azolyl, have now been found.

Furthermore, it has been found that the novel substituted phenoxyphenylsulphonylazoles of the general formula (I) are obtained when (a) in the event that in formula (I) R$^5$ represents hydrogen or nitro and R$^1$, R$^2$, R$^3$, R$^4$, R$^5$ and Az have the abovementioned meanings, substituted phenoxybenzenesulphonyl chlorides of the general formula (II)

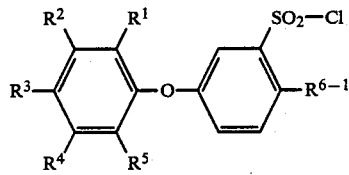

in which
R$^{6-1}$ represents hydrogen or nitro and
R$^1$, R$^2$, R$^3$, R$^4$ and R$^5$ have the abovementioned meanings,
are reacted with azoles of the general formula (III)

   (III)

in which
Az has the abovementioned meaning,
or with alkali metal salts of azoles of the formula (III), if appropriate in the presence of an acid acceptor and if appropriate in the presence of a diluent, or when (b) in the event that in formula (I) R$^6$ represents amino and R$^1$, R$^2$, R$^3$, R$^4$, R$^5$ and Az have the abovementioned meanings, compounds of the general formula (I) in which R$^6$ represents nitro and R$^1$, R$^2$, R$^3$, R$^4$, R$^5$ and Az have the abovementioned meanings, are reacted with hydrogen in the presence of a hydrogenation catalyst and in the presence of a diluent, or when (c) in the event that in the formula (I) R$^6$ represents halogen or cyano and R$^1$, R$^2$, R$^3$, R$^4$, R$^5$ and Az have the abovementioned meanings, compounds of the general (I) in which R$^6$ represents amino and R$^1$, R$^2$, R$^3$, R$^4$, R$^5$ and Az have the abovementioned meanings, are reacted with sodium nitrate or potassium nitrite and with a hydrogen halide (where R$^6$: halogen) or with sulphuric acid (where R$^6$: cyano) in the presence of water and if appropriate in the presence of an organic solvent and the diazonium salt solutions obtained in this process are reacted with aqueous solutions of copper(I) halides or with copper(I) cyanide.

Finally, it has been found that the novel substituted phenoxyphenylsulphonylazoles of the formula (I) show a powerful herbicidal and plant growth regulating action.

Surprisingly, the substituted phenoxyphenylsulphonylazoles of the formula (I) according to the invention have a considerably more powerful effectiveness against weeds than methyl 3-(2,4-dichlorophenoxy)-6-nitro-benzoate, which is a previously known active compound of similar structure and the same direction of action.

The invention preferably relates to compounds of the formula (I) in which
R$^1$ represents hydrogen, halogen, cyano or trifluoromethyl,
R$^2$ represents hydrogen or halogen,
R$^3$ represents halogen, cyano, trifluoromethyl, trifluoromethoxy or trifluoromethylsulphonyl,
R$^4$ represents hydrogen or halogen,
R$^5$ represents hydrogen, or halogen,
R$^6$ represents hydrogen, halogen, cyano, nitro or amino and
Az represents pyrazolyl, imidazolyl or triazolyl, each of which is optionally monosubstituted to trisubstituted by identical or different substitutents from the series comprising halogen, cyano, nitro, amino, C$_1$–C$_4$-alkyl, C$_1$–C$_4$-alkoxy, C$_1$–C$_4$-alkylthio, halogeno-C$_1$–C$_4$-alkyl, halogeno-C$_1$–C$_4$-alkoxy and halogeno-C$_1$–C$_4$-alkylthio.

The invention particularly preferably relates to compounds of the formula (I) in which
R$^1$ represents hydrogen, fluorine, chlorine, bromine, cyano or trifluoromethyl,
R$^2$ represents hydrogen, fluorine, chlorine or bromine,
R$^3$ represents fluorine, chlorine, bromine, cyano, trifluoromethyl, trifluoromethoxy or trifluoromethylsulphonyl,
R$^4$ represents hydrogen, fluorine, chlorine or bromine,
R$^5$ represents hydrogen, fluorine, chlorine or bromine,
R$^6$ represents hydrogen, fluorine, chlorine, bromine, iodine, cyano, nitro or amino and
Az represents pyrazolyl, imidazolyl, or triazolyl, each of which is optionally monosubstituted to trisubstituted by identical or different substituents from the series comprising halogen, cyano, nitro, amino, C$_1$–C$_4$-alkyl, C$_1$–C$_4$-alkoxy, C$_1$–C$_4$- alkylthio, halogeno-$C_1$-$C_4$-alkyl, halogeno-$C_1$-$C_4$-alkoxy and halogeno-$C_1$-$C_4$-alkylthio.

In particular, the invention relates to compounds of the formula (I) in which
$R^1$ represents hydrogen, fluorine or chlorine,
$R^2$ represents hydrogen, fluorine or chlorine,
$R^3$ represents trifluoromethyl,
$R^4$ represents hydrogen, fluorine or chlorine,
$R^5$ represents hydrogen, fluorine or chlorine,
$R^6$ represents hydrogen, chlorine, bromine, cyano, nitro or amino and
Az represents pyrazolyl or imidazolyl, each of which is optionally monosubstituted to trisubstituted by identical or different substituents from the series comprising chlorine, bromine, methyl, ethyl and trifluoromethyl.

Examples of the substituted phenoxyphenylsulphonylazoles are listed in Table 1 below.

TABLE 1

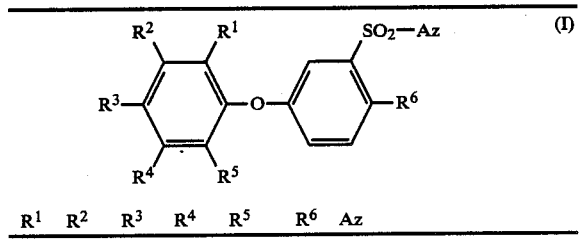

| $R^1$ | $R^2$ | $R^3$ | $R^4$ | $R^5$ | $R^6$ | Az |
|---|---|---|---|---|---|---|
| Cl | H | $CF_3$ | H | H | $NO_2$ | pyrazolyl |
| Cl | H | $CF_3$ | H | Cl | $NO_2$ | pyrazolyl |
| Cl | H | $CF_3$ | H | F | $NO_2$ | pyrazolyl |
| Cl | H | $CF_3$ | Cl | Cl | $NO_2$ | pyrazolyl |
| Cl | H | $CF_3$ | F | Cl | $NO_2$ | pyrazolyl |
| Cl | H | $CF_3$ | H | Cl | $NO_2$ | 3-methylpyrazolyl |
| Cl | H | $CF_3$ | H | F | $NO_2$ | 3-methylpyrazolyl |
| Cl | H | $CF_3$ | H | Cl | $NO_2$ | 4-methylpyrazolyl |
| Cl | H | $CF_3$ | H | F | $NO_2$ | 4-methylpyrazolyl |
| Cl | H | $CF_3$ | H | Cl | $NO_2$ | 4-chloropyrazolyl |
| Cl | H | $CF_3$ | H | Cl | $NO_2$ | 4-bromopyrazolyl |
| Cl | H | $CF_3$ | H | H | $NO_2$ | 3,5-dimethyl... (H3C, CH3) |
| Cl | H | $CF_3$ | H | Cl | $NO_2$ | 3,5-dimethyl... |
| Cl | H | $CF_3$ | H | F | $NO_2$ | 3,5-dimethyl... |
| Cl | H | $CF_3$ | H | Cl | $NO_2$ | 3,4,5-trimethyl... |
| Cl | H | $CF_3$ | H | F | $NO_2$ | 3,4,5-trimethyl... |
| Cl | H | $CF_3$ | H | H | $NO_2$ | 3,4,5-trimethyl... |
| Cl | H | $CF_3$ | H | H | $NO_2$ | 3-methyl-4-chloro... |
| Cl | H | $CF_3$ | H | Cl | $NO_2$ | 3-methyl-4-chloro... |
| Cl | H | $CF_3$ | H | F | $NO_2$ | 3-methyl-4-chloro... |
| Cl | H | $CF_3$ | H | H | $NO_2$ | imidazolyl |

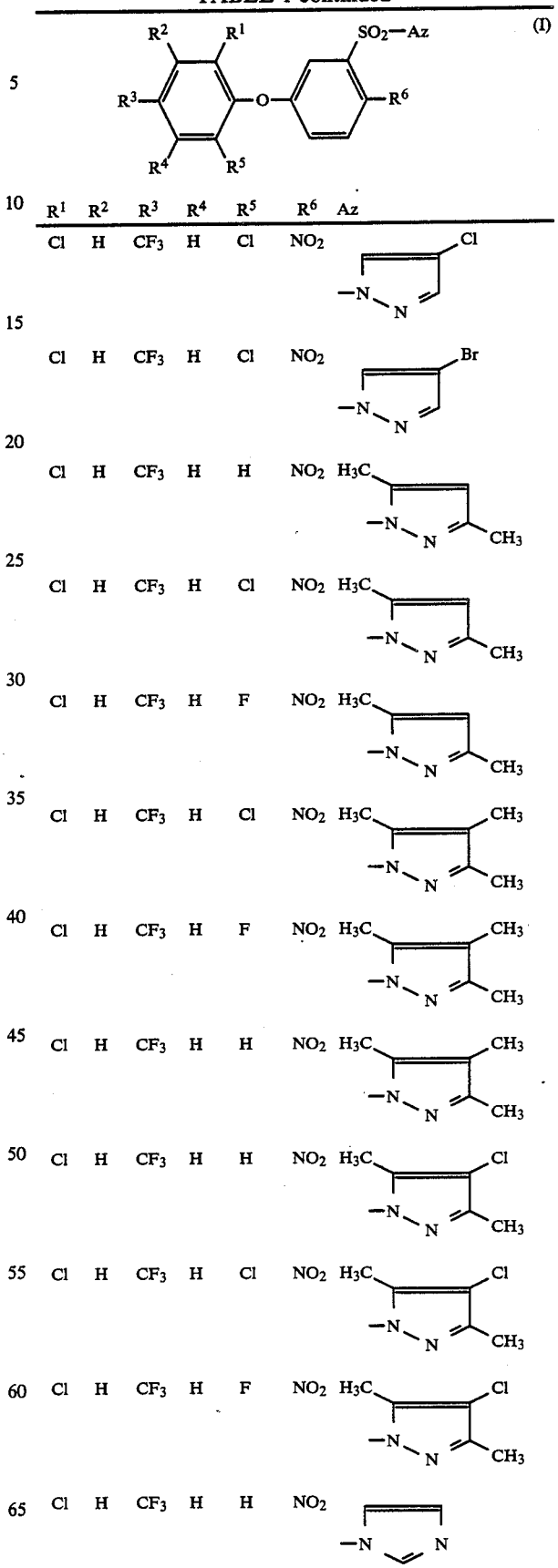

TABLE 1-continued $$\text{R}^2, \text{R}^1, \text{R}^3, \text{R}^4, \text{R}^5 \text{ on phenyl-O-phenyl with } \text{R}^6 \text{ and } SO_2-Az \quad (I)$$

| $R^1$ | $R^2$ | $R^3$ | $R^4$ | $R^5$ | $R^6$ | Az |
|---|---|---|---|---|---|---|
| Cl | H | CF$_3$ | H | Cl | NO$_2$ |  |
| Cl | H | CF$_3$ | H | F | NO$_2$ | 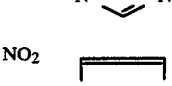 |
| Cl | H | CF$_3$ | H | F | NO$_2$ | 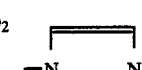 |
| Cl | H | CF$_3$ | H | H | NO$_2$ | 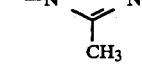 |
| Cl | H | CF$_3$ | H | Cl | NO$_2$ |  |
| Cl | H | CF$_3$ | H | H | NH$_2$ |  |
| Cl | H | CF$_3$ | H | Cl | NH$_2$ | 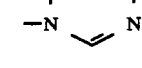 |
| Cl | H | CF$_3$ | H | F | NH$_2$ | 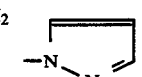 |
| Cl | H | CF$_3$ | Cl | Cl | NH$_2$ |  |
| Cl | H | CF$_3$ | F | Cl | NH$_2$ | 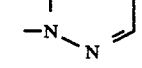 |
| Cl | H | CF$_3$ | H | Cl | NH$_2$ | 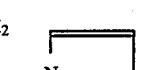 |
| Cl | H | CF$_3$ | H | F | NH$_2$ | 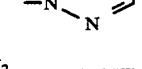 |
| Cl | H | CF$_3$ | H | Cl | NH$_2$ | 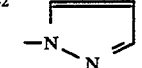 |
| Cl | H | CF$_3$ | H | F | NH$_2$ | 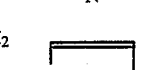 |
| Cl | H | CF$_3$ | H | Cl | NH$_2$ | 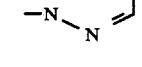 |
| Cl | H | CF$_3$ | H | Cl | NH$_2$ | 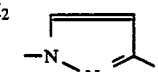 |
| Cl | H | CF$_3$ | H | H | NH$_2$ | 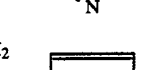 |
| Cl | H | CF$_3$ | H | Cl | NH$_2$ | 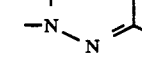 |
| Cl | H | CF$_3$ | H | F | NH$_2$ |  |
| Cl | H | CF$_3$ | H | Cl | NH$_2$ | 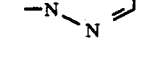 |
| Cl | H | CF$_3$ | H | H | NH$_2$ |  |
| Cl | H | CF$_3$ | H | Cl | NH$_2$ |  |
| Cl | H | CF$_3$ | H | F | NH$_2$ |  |

TABLE 1-continued

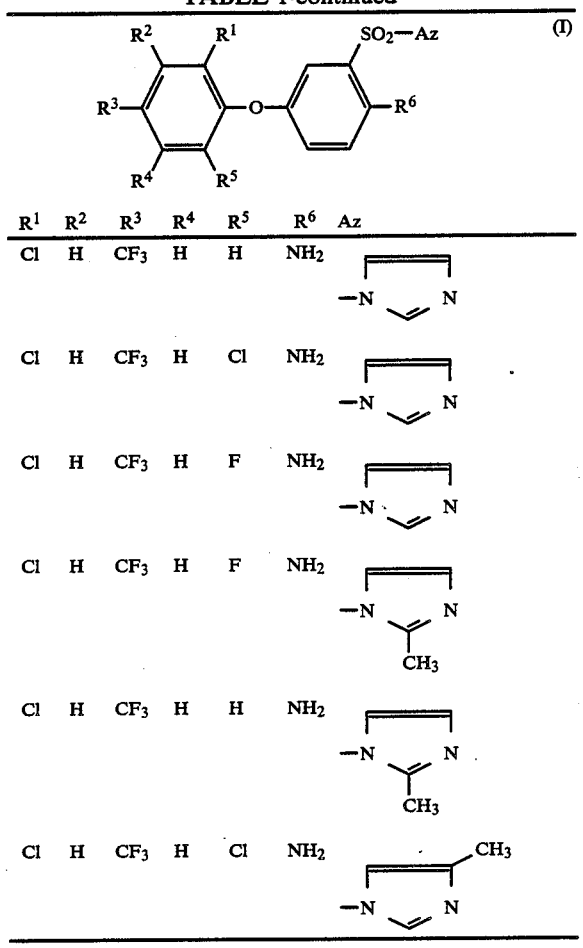

| R¹ | R² | R³ | R⁴ | R⁵ | R⁶ | Az |
|---|---|---|---|---|---|---|
| Cl | H | CF₃ | H | H | NH₂ | -N⌐N (imidazole) |
| Cl | H | CF₃ | H | Cl | NH₂ | -N⌐N (imidazole) |
| Cl | H | CF₃ | H | F | NH₂ | -N⌐N (imidazole) |
| Cl | H | CF₃ | H | F | NH₂ | -N⌐N-CH₃ (2-methylimidazole) |
| Cl | H | CF₃ | H | H | NH₂ | -N⌐N-CH₃ (2-methylimidazole) |
| Cl | H | CF₃ | H | Cl | NH₂ | -N⌐N-CH₃ (2-methylimidazole) |

If, for example, 2-nitro-5-(2,6-difluoro-4-trifluoromethylphenoxy)-benzenesulphonyl chloride and 2-methylimidazole are used as starting materials in process (a) according to the invention, the course of the reaction can be represented by the following equation:

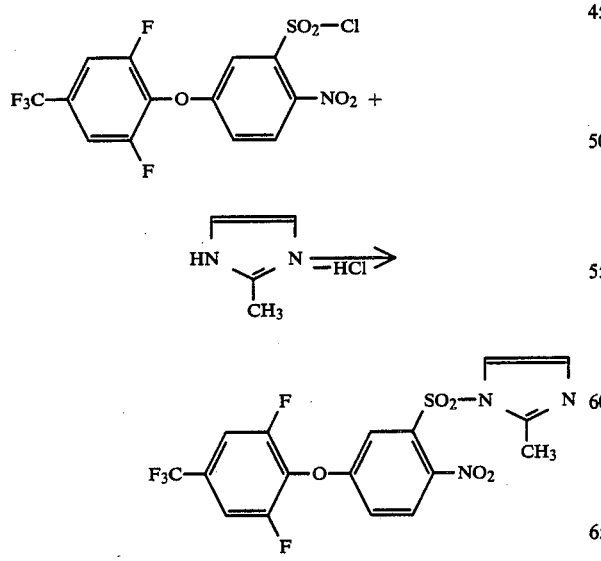

If, for example, (2-nitro-5-(2-chloro-4-trifluoromethylphenoxy)-phenyl-sulphonylpyrazole and hydrogen in the presence of a platinum catalyst are used as starting materials in process (b) according to the invention, the course of the reaction can be represented by the following equation:

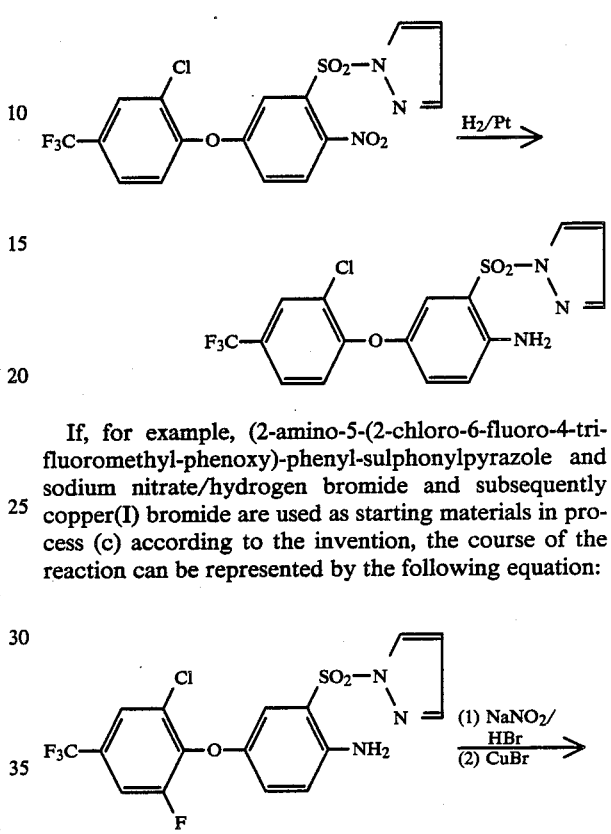

If, for example, (2-amino-5-(2-chloro-6-fluoro-4-trifluoromethyl-phenoxy)-phenyl-sulphonylpyrazole and sodium nitrate/hydrogen bromide and subsequently copper(I) bromide are used as starting materials in process (c) according to the invention, the course of the reaction can be represented by the following equation:

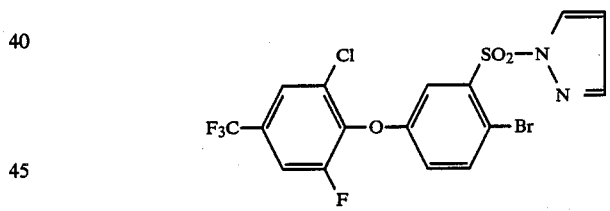

Formula (II) provides a general definition of the substituted phenoxybenzenesulphonyl chlorides to be used as starting materials in process (a) according to the invention for the preparation of compounds of the formula (I).

In formula (II), $R^1$, $R^2$, $R^3$, $R^4$ and $R^5$ preferably, or in particular, have those meanings which have already been mentioned above in connection with the description of the compounds of the formula (I) according to the invention as being preferred, or particularly preferred, for $R^1$, $R^2$, $R^3$, $R^4$ and $R^5$, and $R^{6-1}$ represents hydrogen or nitro.

Examples of the starting materials of the formula (II) which may be mentioned are:

3-(2-chloro-4-trifluoromethyl-phenoxy)-, 3-(2,6-dichloro-4-trifluoromethyl-phenoxy)-, 3-(2-chloro-6-fluoro-4-trifluoromethyl-phenoxy)-3-(2,3,6-trichloro-4-trifluoromethyl)-phenoxy)-and 3-(2,6-dichloro-3-fluoro-4-trifluoromethylphenoxy)-benzenesulphonyl chloride; 2-nitro-5-(2-chloro-4-trifluoromethyl-phenoxy)-, 2-nitro-5-(2,6-dichloro-4-trifluoromethyl-phenoxy-, 2-nitro-5-(2-chloro-6-fluoro-4-trifluoromethyl-phenoxy)-, 2-nitro-5-(2,3,6-trichloro-4-trifluoromethyl-phenoxy)-and2-nitro-5-(2,6-dichloro-3-fluoro-4-trifluoromethyl-phenoxy)-benzenesulphonyl chloride.

The starting materials of the formula (II) are known and/or can be prepared by processes known per se (cf. U.S. Pat. No. 4,213,775).

For example, the compounds of the formula (II) are obtained when (α) in the event that $R^{6-1}$ represents hydrogen, substituted aminodiphenyl ethers of the general formula (IV)

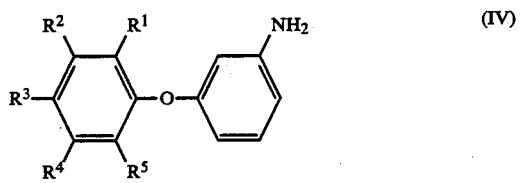

in which $R^1$, $R^2$, $R^3$, $R^4$ and $R^5$ have the abovementioned meanings, are reacted with sodium nitrite or potassium nitrite in the presence of aqueous hydrochloric acid and if appropriate in the presence of an organic solvent, such as, for example, acetic acid, at temperatures between $-10°$ C. and $+20°$ C., and the diazonium salt solutions which are obtained in this process are reacted with sulphur dioxide in the presence of a catalyst, such as, for example, copper(I) chloride and/or copper(II) chloride, at temperatures between $-10°$ C. and $+40°$ C., or when (β) in the event that $R^{6-1}$ represents nitro, substituted dinitrodiphenyl ethers of the general formula (V)

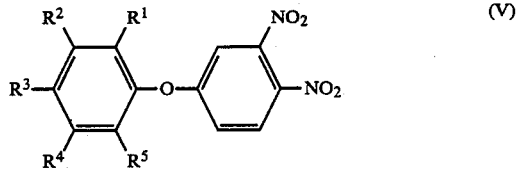

in which $R^1$, $R^2$, $R^3$, $R^4$ and $R^5$ have the abovementioned meanings, are reacted with benzylmercaptan, if appropriate in the presence of an acid acceptor, such as, for example, potassium hydroxide, and if appropriate in the presence of diluents, such as, for example, water, ethanol and isopropanol, at temperatures between 0° C. and 100° C. and the substituted benzylthio-nitro-diphenyl ethers obtained in this process, of the general formula (VI)

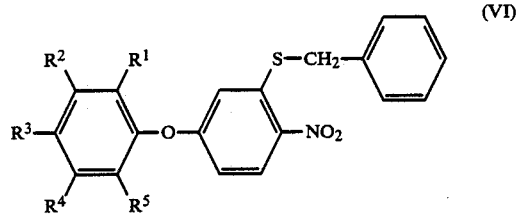

in which $R^1$, $R^2$, $R^3$, $R^4$ and $R^5$ have the abovementioned meanings, are isolated by filtering off with suction and reacted with chlorine in the presence of diluents, such as, for example, water and acetic acid, at temperatures between 0° C. and 50° C.

The intermediates of the formulae (IV) and (V) are known and/or can be prepared by processes known per se (cf. EP-A 29,123; EP-A 7,471).

Formula (III) provides a general definition of the azoles also to be used as starting materials in process (a) according to the invention. In formula (III), Az preferably, or in particular, has the meaning which has already been mentioned above in connection with the description of the compounds of the formula (I) according to the invention as being preferred, or particularly preferred, for Az. Preferred alkali metal salts of the azoles of the formula (III) are the lithium, sodium or potassium salts thereof.

Examples of the starting materials of the formula (III) which may be mentioned are: pyrazole, 4-chloro-pyrazole, 4-bromo-pyrazole, 3-methyl-, 4-methyl-, 3,5-dimethyl- and 3,4,5-trimethyl-pyrazole, 4-chloro-3,5-dimethyl-pyrazole, imidazole, 2-methyl- and 4-methyl-imidazole.

The compounds of the formula (III) are known chemicals for organic synthesis.

Process (a) according to the invention for the preparation of the novel compounds of the formula (I) is preferably carried out using diluents. Suitable diluents for this purpose are virtually all inert organic solvents. These preferably include aliphatic and aromatic, optionally halogenated hydrocarbons, such as pentane, hexane, heptane, cyclohexane, petroleum ether, benzine, ligroin, benzene, toluene, xylene, methylene chloride, ethylene chloride, chloroform, carbon tetrachloride, chlorobenzene and o-dichlorobenzene, ethers, such as diethyl ether and dibutyl ether, glycol dimethyl ether and diglycol dimethyl ether, tetrahydrofuran and dioxane, ketones, such as acetone, methyl ethyl ketone, methyl isopropyl ketone and methyl isobutyl ketone, esters, such as methyl acetate and ethyl acetate, nitriles, such as, for example, acetonitrile and propionitrile, amides, such as, for example, dimethylformamide, dimethylacetamide and N-methyl-pyrrolidone, and also dimethyl sulphoxide, tetramethylene sulphone and hexamethylphosphoric triamide.

Acid acceptors which can be employed in process (a) according to the invention are all acid-binding agents which are customarily used for reactions of this type. Alkali metal hydroxides, such as, for example, sodium hydroxide and potassium hydroxide, alkaline earth metal hydroxides, such as, for example, calcium hydroxide, alkali metal carbonates and alkali metal alkoxides, such as sodium carbonate, potassium carbonate, sodium tert-butoxide and potassium tert-butoxide, furthermore aliphatic, aromatic or heterocyclic amines, for example triethylamine, trimethylamine, dimethylaniline, dimethylbenzylamine, pyridine, 1,5-diazobicyclo-[4,3,0]-non-5-ene (DBN), 1,8-diazabicyclo-[5,4,0]-undec-7-ene (DBU) and 1,4-diazabicyclo-[2,2,2]-octane (DABCO) are preferably suitable.

In process (a) according to the invention, the reaction temperatures can be varied within a relatively wide range. In general, the process is carried out at temperatures between 0° C. and 100° C., preferably at temperatures between 10° C. and 50° C.

Process (a) according to the invention is generally carried out under atmospheric pressure. However, it is also possible to carry out the process under increased or reduced pressure.

For carrying out process (a) according to the invention, the starting materials required in each case are generally employed in approximately equimolar amounts. However, it is also possible to use one of the two components employed in each case in relatively large excess. In general, the reactions are carried out in a suitable diluent in the presence of an acid acceptor, and the reaction mixture is stirred for several hours at the specific temperature required. Working-up in process (a) according to the invention is carried out in each case by customary methods.

Formula (I) provides a general definition of the compounds to be used as starting materials in process (b) according to the invention for the preparation of compounds of the formula (I), with the proviso that $R^6$ in each case represents nitro.

In this case, $R^1$, $R^2$, $R^3$, $R^4$, $R^5$ and Az in formula (I) preferably, or in particular, have those meanings which have already been mentioned above in connection with the compounds of the formula (I) according to the invention as being preferred, or particularly preferred, for $R^1$, $R^2$, $R^3$, $R^4$, $R^5$ and Az.

The starting materials of the formula (I) in process (b) are novel compounds according to the invention; they can be prepared by the processes (a) according to the invention.

Process (b) is carried out using a hydrogenation catalyst. Examples of hydrogenation catalysts which may be mentioned are Raney nickel, platinum and palladium. In process (b), Raney nickel is preferably used.

Process (b) is carried out in the presence of a diluent. Solvents which are preferably employed in process (b) are alcohols, such as methanol, ethanol, propanol or isopropanol, ethers, such as glycol dimethyl ether, diglycol dimethyl ether, tetrahydrofuran or dioxane, or esters, such as methyl acetate or ethyl acetate.

In process (b) according to the invention, the reaction temperatures can be varied within a relatively wide range. The process is generally carried out at temperatures between 0° C. and 150° C., preferably at temperatures between 20° C. and 100° C.

Process (b) is generally carried out under atmospheric pressure or increased pressure up to about 200 bar, preferably up to about 100 bar.

Process (b) can be carried out under the conditions which are customary for catalytic hydrogenations. In a preferred embodiment of process (b), the starting compound of the formula (I) is mixed with the diluent and the catalyst and hydrogen is then metered in until hydrogen uptake can no longer be detected. When the hydrogenation is complete, the reaction mixture is filtered, and, after the filtrate has been concentrated, the crude product is obtained as a residue which can be purified in a customary manner, for example by column chromatography.

Formula (I) provides a general definition of the compounds to be used as starting materials in process (c) according to the invention for the preparation of compounds of the formula (I), with the proviso that $R^6$ in each case represents amino.

In this case, $R^1$, $R^2$, $R^3$, $R^4$, $R^5$ and Az in formula (I) preferably, or in particular, have those meanings which have already been mentioned above in connection with the description of the compounds of the formula (I) according to the invention as being preferred, or particularly preferred, for $R^1$, $R^2$, $R^3$, $R^4$, $R^5$ and Az.

The starting materials of the formula (I) in process (c) are novel compounds according to the invention; they can be prepared by process (b) according to the invention.

Process (c) is carried out using a hydrogen halide or sulphuric acid. Examples of the hydrogen halides which may be mentioned are hydrogen fluoride, hydrogen chloride, hydrogen bromide and hydrogen iodide.

If appropriate, process (c) is carried out using an organic solvent. Examples of organic solvents which are suitable are ethers, such as glycol dimethyl ether and diglycol dimethyl ether, and also tetrahydrofuran and dioxane, ketones, such as acetone and methyl ethyl ketone, and also amides, such as dimethylformamide.

Process (c) is carried out using copper(I) halides or copper(I) cyanide. Examples of the copper(I) halides which may be mentioned are copper(I) chloride, copper(I) bromide and copper(I) iodide.

In process (c) according to the invention, the reaction temperatures can be varied within a relatively wide range. In general, the process is carried out at temperatures between $-20°$ C. and $+80°$ C., preferably at temperatures between 0° C. and 60° C.

In general, process (c) according to the invention is carried out under atmospheric pressure. However, it is also possible to carry out the reaction under increased or reduced pressure.

For carrying out process (c) according to the invention, between 0.8 and 2.5 moles, preferably between 1.1 and 1.5 moles, of sodium nitrite or potassium nitrite and between 2 and 20 moles, preferably between 3 and 10 moles, of hydrogen halide or sulphuric acid, and also between 1 and 3 moles, preferably between 1.1 and 1.5 moles, of copper(I) halide or copper(I) cyanide, are generally employed per mole of starting compound of the formula (I).

First, a diazotization is carried out in a customary manner: for this purpose, the starting compound of the formula (I) is generally first placed in the reaction vessel in an aqueous solution of a hydrogen halide or of sulphuric acid, and an aqueous solution of sodium nitrite or potassium nitrite is slowly added to this solution with cooling. If required, excess nitrous acid is removed after the diazotization using urea, and the diazonium salt solution is added to an aqueous solution of a copper(I) halide or of copper(I) cyanide, with cooling. The mixture is then stirred until the evolution of gas has ceased, if required with heating, and subsequently worked up by customary methods.

The active compounds according to the invention can be used as defoliants, desiccants, agents for destroying broad-leaved plants and, especially, as weedkillers. By weeds, in the broadest sense, there are to be understood all plants which grow in locations where they are undesired. Whether the substances according to the invention act as total or selective herbicides depends essentially on the amount used.

The active compounds according to the invention can be used, for example, in connection with the following plants:

Dicotyledon weeds of the genera: Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver and Centaurea.

Dicotyledon cultures of the genera: Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita.

Monocotyledon weeds of the genera: Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus and Apera.

Monocotyledon cultures of the genera: Oryza, Zea, Triticum, Hordeum, Avena, Secale, Sorghum, Panicum, Saccharum, Ananas, Asparagus and Allium.

However, the use of the active compounds according to the invention is in no way restricted to these genera, but also extends in the same manner to other plants.

The compounds are suitable, depending on the concentration, for the total control of weeds, for example on industrial terrain and rail tracks, and on paths and squares with or without tree plantings. Equally, the compounds can be employed for combating weeds in perennial cultures, for example afforestations, decorative tree plantings, orchards, vineyards, citrus groves, nut orchards, banana plantations, coffee plantations, tea plantations, rubber plantations, oil palm plantations, cocoa plantations, soft fruit plantings and hopfields, and for the selective combating of weeds in annual cultures.

The active compounds of the formula (I) are particularly suitable for selectively controlling dicotyledon weeds in monocotyledon and dicotyledon crops, especially using the post-emergence method.

The active compounds according to the invention engage in the metabolism of the plants and can therefore be employed as growth regulators.

Experience to date of the mode of action of plant growth regulators has shown that an active compound can also exert several different actions on plants. The actions of the compounds depend essentially on the point in time at which they are used, relative to the stage of development of the plant, and on the amounts of active compound applied to the plants or their environment and the way in which the compounds are applied. In every case, growth regulators are intended to influence the crop plants in the particular manner desired.

The amount of leaves on plants can be controlled, under the influence of growth regulators, so that defoliation of the plants at a desired point in time is achieved. Such defoliation is of great importance in the mechanical harvesting of cotton, but is also of interest for facilitating harvesting in other crops, such as, for example, in viticulture. Defoliation of the plants can also be carried out to lower the transpiration of plants before they are transplanted.

The active compounds can be converted into the customary formulations, such as solutions, emulsions, wettable powders, suspensions, powders, dusting agents, pastes, soluble powders, granules, suspension emulsion concentrates, foams, natural and synthetic materials impregnated with active compound as well as very fine capsules in polymeric substances.

These formulations are produced in a known manner, for example by mixing the active compounds with extenders, that is, liquid solvents and/or solid carriers, optionally with the use of surface-active agents, that is, emulsifying agents and/or dispersing agents, and/or foam-forming agents.

In the case of the use of water as an extender, organic solvents can, for example, also be used as auxiliary solvents. As liquid solvents, there are suitable in the main: aromatics, such as xylene, toluene or alkylnaphthalenes, chlorinated aromatics and chlorinated aliphatic hydrocarbons, such as chlorobenzenes, chloroethylenes or methylene chloride, aliphatic hydrocarbons, such as cyclohexane or paraffins, for example mineral oil fractions, mineral and vegetable oils alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water. As solid carriers there are suitable: for example ammonium salts and ground natural minerals, such as kaolins, clays, talc, chalk, quartz, attapulgite, montmorillonite or diatomaceous earth, and ground synthetic minerals, such as highly-disperse silica, alumina and silicates; as solid carriers for granules there are suitable: for example crushed and fractionated natural minerals such as calcite, marble, pumice, sepiolite and dolomite, as well as synthetic granules of inorganic and organic meals, and granules of organic material such as sawdust, coconut shells, corn cobs and tobacco stalks; as emulsifying and/or foam-forming agents there are suitable: for example non-ionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates as well as albumin hydrolysis products; as dispersing agents there are suitable: for example ligninsulphite waste liquors and methylcellulose.

Adhesives such as carboxymethylcellulose, natural and synthetic polymers in the form of powders, granules or latices, such as gum arabic, polyvinyl alcohol and polyvinyl acetate, as well as natural phospholipids, such as cephalins and lecithins, and synthetic phospholipids can be used in the formulations. Further additives may be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95% by weight of active compound, preferably between 0.5 and 90%.

The active compounds according to the invention, as such or in the form of their formulations, can also be used, for combating weeds, as mixtures with known herbicides, finished formulations or tank mixes being possible.

Suitable herbicides for the mixtures are known herbicides, such as, for example, 1-amino-6-ethylthio-3-(2,2-dimethylpropyl)-1,3,5-triazine-2,4(1H,3H)-dione (AMETHYDIONE) or N-(2-benzothiazolyl)-N,N'-dimethylurea (METABENZTHIAZURON) for combating weeds in cereals; 4-amino-3-methyl-6-phenyl-1,2,4-triazine-5(4H)-one (METAMITRON) for combating weeds in sugar beets, and 4-amino-6-(1,1-dimethylethyl)-3-methylthio-1,2,4-triazin -5(4H)-one (METRIBUZIN) for combating weeds in soy beans, furthermore also 2,4-dichlorophenoxyacetic acid (2,4-D); 4-(2,4-dichlorophenoxy)-butyric acid (2,4-DB); 2,4-dichlorophenoxypropionic acid (2,4-DP); 3-isopropyl- 2,1,3-benzothiadiazin-4-one 2,2-dioxide (BENTAZONE); 3,5-dibromo-4-hydroxy-benzonitrile (BROMOXYNIL); 2-chloro-N-{[(4-methoxy-6-methyl-1,3,5-triazin-2-yl)-amino]-carbonyl}-benzenesulphonamide (CHLORSULFURON); N,N-dimethyl-N'-(3-chloro-4-methylphenyl)-urea (CHLORTOLURON); 2-[4-(2,4-dichlorophenoxy)-phenoxy]-propionic acid, its methyl ester or its ethyl ester (DICLOFOP); 4-amino-6-t-butyl-3-ethylthio-1,2,4-triazin-5(4H)-one (ETHIOZIN); 2-{4-[(6-chloro-2-benzoxazolyl)-oxy]-phenoxy)-propanoic acid, its methyl ester or its ethyl ester (FENOXAPROP); [(4-amino-3,5-dichloro-6-fluoro-2-pyridinyl)-oxy]-acetic acid or its 1-methylheptyl ester (FLUROXYPYR); N-phosphonomethyl-glycine (GLYPHOSATE); methyl 2-[4,5-dihydro-4-methyl-4-(1-methylethyl)-5-oxo-1H-imidazol-2-yl]-4(5)-methylbenzoate (IMAZAMETHABENZ); 3,5-diiodo-4-hydroxybenzonitrile(IOXYNIL);N,N-dimethyl-N'-(4-isopropylphenyl)-urea (ISOPROTURON); (2-methyl-4-chlorophenoxy)-acetic acid (MCPA); (4-chloro-2-methylphenoxy)-propionic acid (MCPP); N-methyl-2-(1,3-benzo-thiazol-2-yloxy)-acetanilide (MEFENACET); 2-{[[((4-methoxy-6-methyl-1,3,5-triazin-2-yl)-amino)-carbonyl]-amino]-sulphonyl}-benzoic acid or its methyl ester (METSULFURON); N-(1-ethylpropyl)-3,4-dimethyl-2,6-dinitro-aniline (PENDIMETHALIN);O-(6-chloro-3-phenyl-pyridazin-4-yl) S-octyl thiocarbonate (PYRIDATE); 4-ethylamino-2-t-butylamino-6-methylthio-s-triazine (TERBUTRYNE) and methyl 3-[[[[(4-methoxy-6-methyl-1,3,5-triazin-2-yl)-amino]-sulphonyl]-thiophene-2-carboxylate (THIAMETURON). Surprisingly, some mixtures also show a synergistic action.

Mixtures with other known active compounds, such as fungicides, insecticides, acaricides, nematicides, bird repellents, plant nutrients and agents which improve soil structure, are also possible.

The active compounds can be used as such, in the form of their formulations or in the use forms prepared therefrom by further dilution, such as ready-to-use solutions, suspensions, emulsions, powders, pastes and granules. They are used in the customary manner, for example by watering, spraying, atomizing or scattering.

The active compounds according to the invention can be applied either before or after emergence of the plants.

They can also be incorporated into the soil before sowing.

The amount of active compound used can vary within a substantial range. It depends essentially on the nature of the desired effect. In general, the amounts used are between 0.01 and 15 kg of active compound per hectare of soil surface preferably between 0.05 and 10 kg per ha.

The preparation and the use of the active compounds according to the invention can be seen from the Examples which follow.

Preparation Examples

EXAMPLE 1

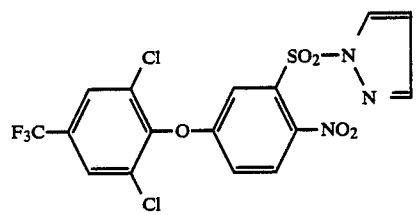

(Process (a))

A solution of 6.0 g (0.013 mol) of 2-nitro-5-(2,6-dichloro-4-trifluoromethyl-phenoxy)-benzenesulphonyl chloride in 30 ml of methylene chloride is added to a stirred mixture of 0.9 g (0.013 mol) of pyrazole, 1.3 g (0.016 mol) of pyridine and 30 ml of methylene chloride, and the reaction mixture is stirred for 15 hours at 20° C. It is then acidified using 2N hydrochloric acid, and the organic phase is separated off, dried using sodium sulphate and filtered. The solvent is carefully distilled off from the filtrate under a water pump vacuum.

3.8 g (61% of theory) of (2-nitro-5-(2,6-dichloro-4-trifluoromethyl-phenoxy)-phenyl)-sulphonylpyrazole are obtained as a crystalline residue of melting point 159° C.

EXAMPLE 2

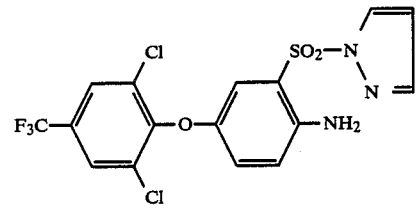

(Process (b))

2.4 g (5 mmol) of (2-nitro-5-(2,6-dichloro-4-trifluoromethylphenoxy)-phenyl)-sulphonylpyrazole are dissolved in 100 ml of methanol and, after the addition of 2 g of Raney nickel, hydrogenated at 30° C. under a hydrogen pressure of 20 to 30 bar. The mixture is then filtered, the filtrate is concentrated, and the residue is stirred with isopropanol. The crystalline product which is obtained in this process is isolated by filtering off with suction.

0.5 g (22% of theory) of (2-amino-5-(2,6-dichloro-4-trifluoromethyl-phenoxy)-phenyl)-sulphonylpyrazole of melting point 232° C. are obtained.

The compounds of the formula (I) listed in Table 2 below can be obtained analogously to Examples 1 and 2 and following the general description of the preparation processes according to the invention.

TABLE 2

Preparation examples of the compounds of formula (I)

$$\text{(I)} \quad R^2\text{-}R^1\text{-phenyl-O-phenyl(}R^6\text{)-SO}_2\text{-Az}$$

with substituents $R^1, R^2, R^3, R^4, R^5$ on the left ring and $SO_2\text{-Az}$, $R^6$ on the right ring.

| Ex. No. | $R^1$ | $R^2$ | $R^3$ | $R^4$ | $R^5$ | $R^6$ | Az | Physical data |
|---|---|---|---|---|---|---|---|---|
| 3 | Cl | H | $CF_3$ | H | Cl | $NO_2$ | 3,5-dimethylpyrazol-1-yl | $n_D^{20}$: 1.5611 |
| 4 | Cl | H | $CF_3$ | H | Cl | H | pyrazol-1-yl | m.p. 141° C. |
| 5 | Cl | H | $CF_3$ | H | Cl | H | 3-methylpyrazol-1-yl | m.p. 118° C. |
| 6 | Cl | H | $CF_3$ | H | H | H | 3,5-dimethylpyrazol-1-yl | m.p. 103° C. |
| 7 | Cl | H | $CF_3$ | H | Cl | $NO_2$ | 3-methylpyrazol-1-yl | m.p. 153° C. |
| 8 | Cl | H | $CF_3$ | H | Cl | $NO_2$ | 4-trifluoromethylimidazol-1-yl | m.p. 154° C. |
| 9 | Cl | H | $CF_3$ | H | F | $NO_2$ | 3,5-dimethylpyrazol-1-yl | — |
| 10 | Cl | H | $CF_3$ | H | Cl | $NO_2$ | 4-bromo-3,5-dimethylpyrazol-1-yl | — |
| 11 | Cl | H | $CF_3$ | H | Cl | $NH_2$ | 3,5-dimethylpyrazol-1-yl | m.p. 163° C. |

Starting materials of the formula (II)

EXAMPLE (II-1)

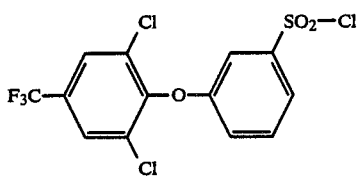

A solution of 34 g (0.49 mol) of sodium nitrite in 50 ml of water is added dropwise, with stirring and cooling at 0° C., to a mixture of 145 g (0.45 mol) of 3-(2,6-dichloro-4-trifluoromethyl-phenoxy)-aniline, 120 ml of acetic acid and 160 ml of concentrated hydrochloric acid. The mixture is stirred for 90 minutes at 0° C., 5 g of sulphamic acid are added, the mixture is then stirred for a further 15 minutes at 0° C. and then added to 400 ml of acetic acid which has previously been saturated with sulphur dioxide. After the addition of 9 g of copper(II) chloride, dissolved in 10 ml of water, the mixture is stirred for 15 hours at 10° C. to 20° C. and then poured on ice. The mixture is extracted with methylene chloride, and the organic phase is dried using sodium sulphate and filtered. The solvent is carefully distilled off from the filtrate under a water pump vacuum.

108 g (59% of theory) of 3-(2,6-dichloro-4-trifluoromethyl-phenoxy)-benzenesulphonyl chloride are obtained as a brown-yellow oily residue.

EXAMPLE (II-2)

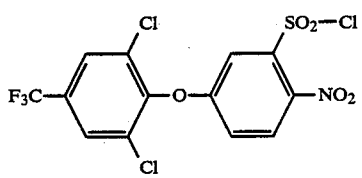

A solution of 3.0 g (0.05 mol) of potassium hydroxide in 7 ml of ethanol/2 ml of water is added dropwise and with stirring to a mixture of 15.9 g (0.04 mol) of 1,2-dinitro-4-(2,6-dichloro-4-(trifluoromethyl-phenoxy)-benzene, 5.6 g (0.045 mol) of benzylmercaptan and 140 ml of isopropanol, and the mixture is refluxed for 3 hours. The crystalline product which is obtained after cooling is isolated by filtering off with suction.

14.5 g (78.5% of theory) of 1-nitro-2-benzylthio-4-(2,6-dichloro-4-trifluoromethyl-phenoxy)-benzene of melting point 207° C. are obtained.

The entire amount of the product obtained in this manner (14.5 g, 0.03 mol) is taken up in 120 ml of acetic acid/20 ml of water, and chlorine is introduced at 12° C. until the mixture is saturated. The reaction mixture is allowed to stand for 15 hours at 20° C., then diluted with water and extracted with toluene, and the organic phase is dried using sodium sulphate and filtered. The solvent is carefully distilled off from the filtrate under a water pump vacuum.

12.5 g (93% of theory) of 2-nitro-5-(2,6-dichloro-4-trifluoromethyl-phenoxy)-benzenesulfonyl chloride are obtained as a brown-yellow oily residue.

USE EXAMPLES

In the Use Examples which follow, the compound listed below is used as comparison substance:

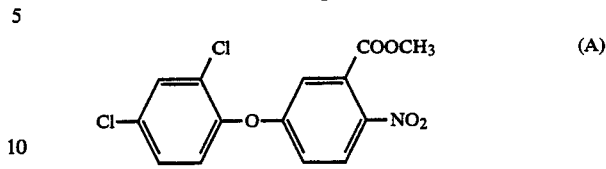

Methyl 3-(2,4-dichloro-phenoxy)-6-nitrobenzoate (disclosed in specification U.S. Pat. No. 3,652,645 and specification U.S. Pat. No. 3,776,715).

EXAMPLE A

Post-emergence test
Solvent: 5 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

Test plants which have a height of 5-15 cm are sprayed with the preparation of the active compound in such a way as to apply the particular amounts of active compound desired per unit area. The concentration of the spray liquor is so chosen that the particular amounts of active compound desired are applied in 2,000 l of water/ha. After three weeks, the degree of damage to the plants is rated in % damage in comparison to the development of the untreated control. The figures denote:

0% = no action (like untreated control)
100% = total destruction

In this test, for example the compounds according to Preparation Examples (1), (3) and (7) show a clearly superior effectiveness compared with comparison substance (A).

EXAMPLE B

Defoliation and desiccation of the leaves of cotton

Solvent: 30 parts by weight of dimethylformamide
Emulsifier: 1 part by weight of polyoxyethylene sorbitan monolaurate To produce a suitable preparation of active compound, 1 part by weight of active compound is mixed with the stated amounts of solvent and emulsifier and the mixture is made up to the desired concentration with water.

Cotton plants are grown in a greenhouse until the 5th true leaf has unfolded completely. At this stage, the plants are sprayed with the preparations of active compound until dripping wet. After 1 week, the shedding of leaves and the desiccation of the leaves are rated, in comparison with the control plants.

In this test, for example the active compounds according to Preparation Examples (1) and (3) show a very severe desiccation of the leaves and a very severe shedding of leaves.

It will be understood that the specification and examples are illustrative but not limitative of the present invention and that other embodiments within the spirit and scope of the invention will suggest themselves to those skilled in the art.

We claim:

1. A substituted phenoxyphenylsulphonylazole of the formula,

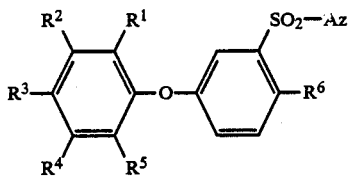

in which
R¹ represents hydrogen, halogen, cyano or trifluoromethyl,
R² represents hydrogen or halogen,
R³ represents halogen, cyano, trifluoromethyl, trifluoromethoxy or trifluoromethylsulphonyl,
R⁴ represents hydrogen or halogen,
R⁵ represents hydrogen or halogen,
R⁶ represents hydrogen, halogen, cyano, nitro or amino and
Az represents optionally substituted pyrazolyl.

2. A substituted phenoxyphenylsulphonylazole according to claim 1, in which
R¹ represents hydrogen, halogen, cyano or trifluoromethyl,
R² represents hydrogen or halogen,
R³ represents halogen, cyano, trifluoromethyl, trifluoromethoxy or trifluoromethylsulphonyl,
R⁴ represents hydrogen or halogen,
R⁵ represents hydrogen, or halogen,
R⁶ represents hydrogen, halogen, cyano, nitro or amino and
Az represents pyrazolyl which is optionally monosubstituted to trisubstituted by identical or different substitutents from the group consisting of halogen, cyano, nitro, amino, $C_1$-$C_4$-alkyl, $C_1$-$C_4$-alkoxy, $C_1$-$C_4$-alkylthio, halogeno-$C_1$-$C_4$-alkyl, halogeno-$C_1$-$C_4$-alkoxy and halogeno-$C_1$$C_4$-alkylthio.

3. A substituted phenoxyphenylsulphonylazole according to claim 1, in which
R¹ represents hydrogen, fluorine, chlorine, bromine, cyano or trifluoromethyl,
R² represents hydrogen, fluorine, chlorine or bromine,
R³ represents fluorine, chlorine, bromine, cyano, trifluoromethyl, trifluoromethoxy or trifluoromethylsulphonyl,
R⁴ represents hydrogen, fluorine, chlorine or bromine,
R⁵ represents hydrogen, fluorine, chlorine or bromine,
R⁶ represents hydrogen, fluorine, chlorine, bromine, iodine, cyano, nitro or amino and
Az represents pyrazolyl which is optionally monosubstituted to trisubstituted by identical or different substituents from the group consisting of halogen, cyano, nitro, amino, $C_1$-$C_4$-alkyl, $C_1$-$C_4$-alkoxy, $C_1$-$C_4$-alkylthio, halogeno-$C_1$-$C_4$-alkyl, halogeno-$C_1$-$C_4$-alkoxy and halogeno-$C_1$-$C_4$-alkylthio.

4. A substituted phenoxyphenylsulphonylazole according to claim 1, in which
R¹ represents hydrogen, fluorine or chlorine,
R² represents hydrogen, fluorine or chlorine,
R³ represents trifluoromethyl,
R⁴ represents hydrogen, fluorine or chlorine,
R⁵ represents hydrogen, fluorine or chlorine,
R⁶ represents hydrogen, chlorine, bromine, cyano, nitro or amino and
Az represents pyrazolyl which is optionally monosubstituted to trisubstituted by identical or different substituents from the group consisting of chlorine, bromine, methyl, ethyl and trifluoromethyl.

5. A compound according to claim 1, wherein such compound is (2-nitro-5-(2,6-dichloro-4-trifluoromethyl-phenoxy)-phenyl)-sulphonyl-pyrazole of the formula

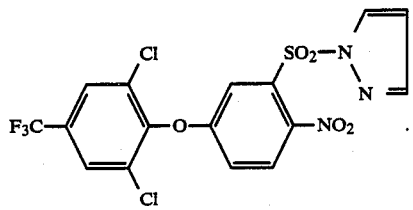

6. A compound according to claim 1, wherein such compound is (2-nitro-5-(2,6-dichloro-4-trifluoromethyl-phenoxy)-phenyl)-sulphonyl-3,5-dimethyl pyrazole of the formula

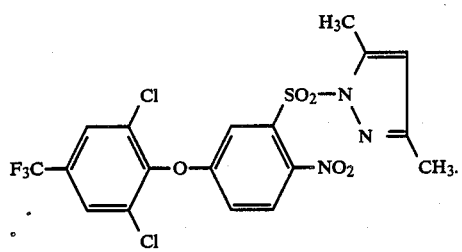

7. A compound according to claim 1, wherein such compound is (2-nitro-5-(2,6-dichloro-4-trifluoromethyl-phenoxy)-phenyl)-sulphonyl-3-methyl-pyrazole of the formula

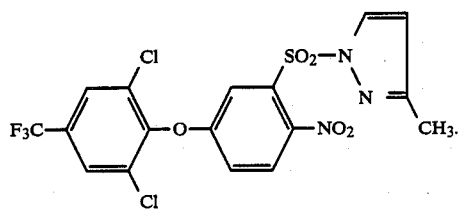

8. A herbicidal composition comprising a herbicidally effective amount of a compound according to claim 1 and a diluent.

9. A method of combating unwanted vegetation which comprises applying to such vegetation or to a locus from which it is desired to exclude such vegetation a herbicidally effective amount of a compound according to claim 1.

10. The method according to claim 9, wherein such compound is
(2-nitro-5-(2,6-dichloro-4-trifluoromethyl-phenoxy)-phenyl)-sulphonyl-pyrazole,
(2-nitro-5-(2,6-dichloro-4-trifluoromethyl-phenoxy)-phenyl)-sulphonyl-3,5-dimethyl pyrazole or
(2-nitro-5-(2,6-dichloro-4-trifluoromethyl-phenoxy)-phenyl)-sulphonyl-3-methyl-pyrazole.

11. A plant growth-regulating composition comprising a plant growth-regulating effective amount of a compound according to claim 1 and a diluent.

12. A method of regulating the growth of a plant which comprises applying to such plant or to a locus in which said plant is growing or is to be grown a plant growth-regulating effective amount of a compound according to claim 1.

13. A method of regulating the growth of a plant which comprises applying to such plant or to a locus in which said plant is growing or is to be grown a plant growth-regulating effective amount of a compound according to claim 12.

* * * * *